United States Patent
Miura et al.

(10) Patent No.: US 10,894,759 B2
(45) Date of Patent: Jan. 19, 2021

(54) METHOD AND APPARATUS FOR PRODUCING ACETIC ACID

(71) Applicant: Daicel Corporation, Osaka (JP)

(72) Inventors: Hiroyuki Miura, Himeji (JP); Yoshihisa Mizutani, Himeji (JP)

(73) Assignee: DAICEL CORPORATION, Osaka (JP)

(*) Notice: Subject to any disclaimer, the term of this patent is extended or adjusted under 35 U.S.C. 154(b) by 0 days.

(21) Appl. No.: 16/542,858

(22) Filed: Aug. 16, 2019

(65) Prior Publication Data

US 2019/0367439 A1 Dec. 5, 2019

Related U.S. Application Data

(62) Division of application No. 15/751,959, filed as application No. PCT/JP2016/077874 on Sep. 21, 2016, now Pat. No. 10,428,006.

(30) Foreign Application Priority Data

Sep. 30, 2015 (JP) .................................. 2015-194762

(51) Int. Cl.
*C07C 51/12* (2006.01)
*B01D 3/14* (2006.01)
(Continued)

(52) U.S. Cl.
CPC .............. *C07C 51/12* (2013.01); *B01D 3/143* (2013.01); *B01D 3/148* (2013.01); *B01D 3/40* (2013.01);
(Continued)

(58) Field of Classification Search
CPC ......... C07C 51/12; C07C 51/44; C07C 53/08; B01D 3/40; B01D 3/143; B01D 3/148; B01D 5/006; B01D 3/42
See application file for complete search history.

(56) References Cited

U.S. PATENT DOCUMENTS

| 5,625,095 A | 4/1997 | Miura et al. |
| 2005/0197508 A1 | 9/2005 | Scates et al. |
| (Continued) | | |

FOREIGN PATENT DOCUMENTS

| CN | 101380522 A | 3/2009 |
| JP | 8-067650 A | 3/1996 |
| (Continued) | | |

OTHER PUBLICATIONS

English translation of International Preliminary Report on Patentability and Written Opinion dated Apr. 12, 2018, in PCT International Application No. PCT/JP2016/077874.
(Continued)

*Primary Examiner* — Yate' K Cutliff
(74) *Attorney, Agent, or Firm* — Birch, Stewart, Kolasch & Birch, LLP

(57) ABSTRACT

A process for stably and safely producing acetic acid without increasing an internal pressure of a distillation column is provided. The process comprises (1) a carbonylation reaction step for allowing methanol to react with carbon monoxide; (2) a flash step for separating the reaction mixture into a volatile phase and a less-volatile phase; (3) a first distillation step for separating the volatile phase into a first overhead and a crude acetic acid stream rich in acetic acid; and (4) a separation step for separating at least acetaldehyde from the first overhead. The separation step (4) comprises (6) a second distillation step for distilling the first overhead while controlling an internal pressure of a distillation column provided with a pressure control unit 68 to form a second overhead rich in acetaldehyde and methyl iodide and a bottom or lower stream, and (7) an extraction step for extracting acetaldehyde from the second overhead to form an extract rich in acetaldehyde and a raffinate rich in methyl iodide.

17 Claims, 1 Drawing Sheet

(51) Int. Cl.
    *C07C 51/44*   (2006.01)
    *C07C 53/08*   (2006.01)
    *B01D 3/40*    (2006.01)
    *B01D 5/00*    (2006.01)
    *B01D 3/42*    (2006.01)

(52) U.S. Cl.
    CPC .............. *B01D 5/006* (2013.01); *C07C 51/44* (2013.01); *C07C 53/08* (2013.01); *B01D 3/4294* (2013.01)

(56) References Cited

U.S. PATENT DOCUMENTS

| | | |
|---|---|---|
| 2005/0197509 A1 | 9/2005 | Picard et al. |
| 2006/0247466 A1 | 11/2006 | Zinobile et al. |
| 2008/0103335 A1 | 5/2008 | Scates et al. |
| 2009/0088587 A1 | 4/2009 | Powell |
| 2009/0270650 A1 | 10/2009 | Patt |
| 2010/0249453 A1 | 9/2010 | Hallinan et al. |
| 2015/0025270 A1 | 1/2015 | Shimizu et al. |
| 2015/0299084 A1 | 10/2015 | Shimizu et al. |

FOREIGN PATENT DOCUMENTS

| | | | |
|---|---|---|---|
| JP | H09-29001 A | 2/1997 | |
| JP | 3244385 B2 | 1/2002 | |
| JP | 2007-222846 A | 9/2007 | |
| JP | 2007-526305 A | 9/2007 | |
| JP | 2007-526310 A | 9/2007 | |
| JP | 2011-256157 A | 12/2011 | |
| KR | 10-2014-0135239 A | 11/2014 | |
| NZ | 584011 A | 10/2012 | |
| RU | 2011143873 A | 5/2013 | |
| WO | WO 2014/097867 A1 * | 6/2014 | ............ C07C 51/12 |
| WO | WO 2014/097867 A1 | 6/2014 | |

OTHER PUBLICATIONS

International Search Report (PCT/ISA/210) issued in PCT/JP2016/077874, dated Nov. 8, 2016.
Written Opinion (PCT/ISA/237) issued in PCT/JP2016/077874, dated Nov. 8, 2016.
Office Action dated Sep. 15, 2020 for Japanese Patent Application No. 2017-543190.
Chinese Office Action for Chinese Application No. 201680057961.3, dated Jun. 30, 2020, with an English translation.
Indian Office Action for Application No. 201817007368, dated Aug. 20, 2020, with English language translation.

* cited by examiner

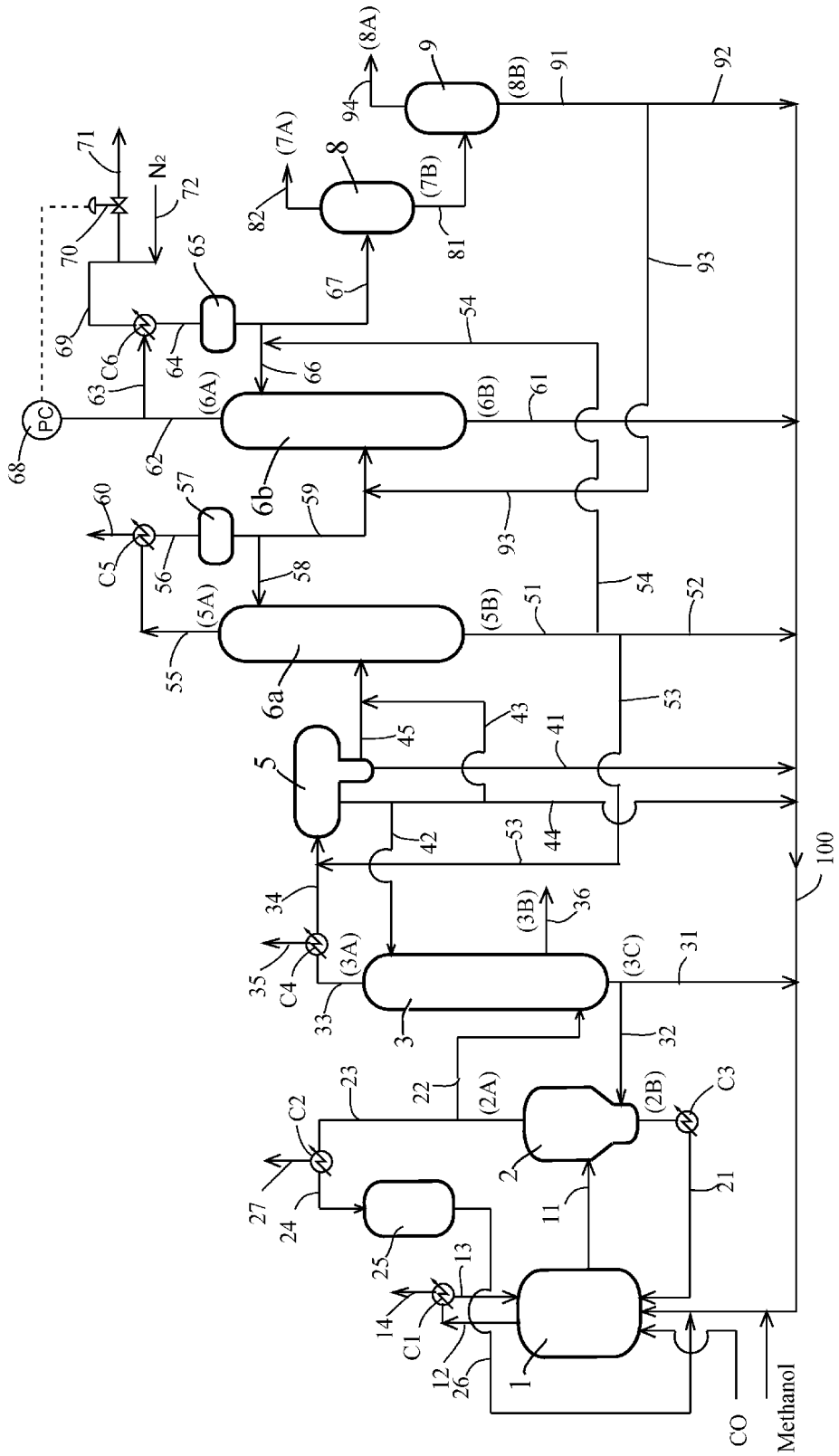

METHOD AND APPARATUS FOR PRODUCING ACETIC ACID

CROSS REFERENCE TO RELATED APPLICATIONS

This application is a Divisional of copending application Ser. No. 15/751,959, filed on Feb. 12, 2018, which is a national phase of PCT International Application No. PCT/JP2016/077874 filed on Sep. 21, 2016, which claims the benefit under 35 U.S.C. § 119(a) to Patent Application No. 2015-194762, filed in Japan on Sep. 30, 2015, all of which are hereby expressly incorporated by reference into the present application.

TECHNICAL FIELD

The present invention relates to processes and apparatuses for effectively producing acetic acid by a methanol carbonylation while removing acetaldehyde.

BACKGROUND ART

Acetic acid is produced industrially by carbonylating methanol in the presence of water, a rhodium catalyst, a metal iodide, and methyl iodide. In the methanol-carbonylation process, acetaldehyde is separated and removed by using process units including a reactor for carbonylating methanol in a carbon monoxide atmosphere, an evaporator for separating the reaction mixture fed from the reactor into a volatile phase and a less-volatile phase, a splitter column for distilling the volatile phase to form a first overhead and a side-cut acetic acid stream, a decanter for condensing the first overhead to forma condensate biphasically separated into a liquid heavy phase and a liquid light phase, a distillation column for distilling the condensate fed from the decanter to form a second overhead and a bottom stream, a condenser for condensing the second overhead, and an extractor for extracting water-soluble impurities from the condensate with water form a raffinate and a water extract.

On the separation of acetaldehyde, Japanese Patent No. 3244385 (JP-3244385B, Patent Document 1) discloses a process for producing acetic acid, in which the reaction of methanol with carbon monoxide is carried out while maintaining an acetaldehyde concentration in the reaction liquid at 400 ppm or lower by removing acetaldehyde from a process liquid being circulated into a reactor. This document describes that a second overhead was subjected to water extraction with theoretical two stages to remove acetaldehyde from the process liquid and the resulting raffinate is recycled to the reactor.

According to the process, because the process stream in which acetaldehyde has been removed is recycled to the reactor, the acetaldehyde concentration in the reaction liquid can be reduced to prevent or reduce the formation of by-products.

Japanese Patent Application Laid-Open Publication No. 2007-526305 (JP-2007-526305A, Patent Document 2) discloses a process which comprises subjecting a second overhead rich in a permanganate reducing compound (PRC) with water and separating therefrom an aqueous stream, and, in order to improve aldehyde removal efficiency, recycling a first portion of the extracted raffinate to a distillation column and recycling a second portion of the raffinate to a reactor.

Japanese Patent Application Laid-Open Publication No. 2007-526310 (JP-2007-526310A, Patent Document 3) discloses twice extraction of a second overhead rich in a permanganate reducing compound (PRC) with water. The document also discloses recycling of a raffinate to a reactor and depicts recycling of a portion of the raffinate to a distillation column in drawings.

According to the processes described in Patent Documents 2 and 3, recycling dimethyl ether (DME) together with the raffinate described above to the reactor allows DME to be consumed as a raw material of acetic acid in the reactor and to prevent the inoperativeness of the process, although DME contained in a process liquid from the distillation column and DME produced in the distillation column significantly increase the pressure of the distillation column (the pressure of the column top) over a long period of time. However, according to these processes, despite precedent concentration of acetaldehyde, the high concentration of acetaldehyde is returned to the reactor, and thus the removal amount of acetaldehyde is reduced. Such an operation not only reduces the acetaldehyde removal efficiency but also increases the acetaldehyde concentration in the reaction liquid to increase the formation of acetaldehyde-derived impurities (for example, propionic acid, hexyl iodide, and crotonaldehyde). Thus, in order to improve the quality of acetic acid, it is necessary to increase an apparatus for reducing or removing substances such as propionic acid, permanganate reducing compounds (PRC's), and iodides.

CITATION LIST

Patent Literature

Patent Document 1: JP-3244385B (claim 2 and Examples)
Patent Document 2: JP-2007-526305A (claim 1, [0045], [0046], and FIG. 2)
Patent Document 3: JP-2007-526310A (claims 1 and 5, [0044], and FIG. 2)

SUMMARY OF INVENTION

Technical Problem

It is therefore an object of the present invention to provide a process and an apparatus for producing acetic acid, which are stably and safely operable without increasing an internal pressure of a distillation column.

Another object of the present invention is to provide a process and an apparatus for producing acetic acid with improving acetaldehyde removal efficiency.

It is still another object of the present invention to provide a process and an apparatus for producing acetic acid, in which DME contained in an off-gas from a top of a column is reused effectively.

Solution to Problem

The inventors of the present invention made intensive studies to achieve the above objects and finally found that (i) a pressure control unit disposed or arranged to a top of a distillation column allows stable and safe distillation operation without increasing the internal pressure of the distillation column (increasing the pressure of the column top) even if a process stream containing DME having a high vapor pressure is distilled, (ii) such an operation does not necessarily have to recycle a process stream in which acetaldehyde is concentrated to a reactor, and thus achieves an improved acetaldehyde removal efficiency, and (iii) a useful component is effectively utilizable by treating an off-gas obtained from the top of the distillation column to recover the useful component and recycling the useful component to the reactor and/or the distillation column. The present invention was accomplished based on the above findings.

That is, an aspect of the present invention provides a process for producing a purified acetic acid by methanol carbonylation. The process comprises (1) a carbonylation reaction step for allowing methanol to react with carbon monoxide in the presence of a catalyst system, acetic acid, methyl acetate, and water, wherein the catalyst system comprises a metal catalyst, an ionic metal iodide, and methyl iodide; (2) a flash step for separating the reaction mixture into a volatile phase and a less-volatile phase; (3) a first distillation step for separating the volatile phase into a first overhead and a crude acetic acid stream, wherein the first overhead is rich in at least one lower boiling point component selected from the group consisting of methyl iodide and acetaldehyde, the crude acetic acid stream is rich in acetic acid; and (4) a separation step for separating at least acetaldehyde from the first overhead. The separation step (4) comprises (6) a second distillation step for distilling the first overhead while controlling an internal pressure of a distillation column to form a second overhead rich in acetaldehyde and methyl iodide and a bottom or lower stream, and (7) an extraction step for extracting acetaldehyde from the second overhead to form an extract rich in acetaldehyde and a raffinate rich in methyl iodide. This process achieves stable and safe operation by a pressure control unit disposed or arranged at the distillation column for distilling the first overhead even if the internal pressure of the distillation column (in particular, the pressure of the column top) in the second distillation step is increased.

The separation step (4) may comprise (5) a step for condensing the first overhead to form a first condensate (or a step for biphasically separating the first condensate into an upper aqueous phase and a lower organic phase) (a step for forming a first condensate and separating the first condensate into two phases of an upper phase and a lower phase, as a mixture), and the first condensate (the upper phase and/or the lower phase) may be distilled in the second distillation step (6). For example, in the condensation or liquid-liquid separation step, (5) the first overhead may be condensed to form the first condensate (or two phases), and at least a portion of the upper phase and/or the lower phase may be distilled in the second distillation step (6) while controlling the internal pressure of the distillation column. Moreover, at least the lower phase may be distilled in the second distillation step (6) while controlling the internal pressure of the distillation column. The internal pressure of the distillation column in the second distillation step (6) may be, for example, about 0.1 to 0.7 MPa in terms of absolute pressure.

Further, the second distillation step (6) may comprise a plurality of distillation steps (continuous distillation steps by plural distillation columns). The first overhead may be distilled while controlling an internal pressure of a distillation column in at least a downstream distillation step.

Furthermore, the process may comprise a step for condensing the second overhead from the second distillation step or the second distillation column (6) to form a second condensate and an off-gas. The second condensate may be subject to the extraction step (7). The off-gas from the second overhead may be discharged to the outside of the system, or (10) a useful component in the off-gas may be directly or indirectly recycled to the reaction step and/or the distillation step(s) (the first distillation step (3) and/or the second distillation column (6)). For example, the off-gas may be condensed to form a third condensate, and the third condensate may be recycled to the reaction step and/or the distillation step(s). More specifically, in cooling and condensing the first overhead in a plurality of condensers which are sequentially lower in condensation temperature with more downstream direction, the off-gas from at least the second overhead may be fed upstream of the plurality of condensers or between the plurality of condensers, and the resulting condensation fraction (condensate) may be recycled to the reaction step and/or distillation step(s) (the first distillation step (3) and/or the second distillation column (6)). Moreover, a valuable resource (a useful component) may be recovered from the off-gas by using a scrubbing apparatus and may be recycled to the reaction step and/or the distillation step(s) (the first distillation step (3) and/or the second distillation column (6)). More specifically, the off-gas may be absorbed to an absorption solvent under an applied pressure, and at least one component selected from the group consisting of methyl iodide, methyl acetate, dimethyl ether, water, and carbon monoxide may be diffused from the resulting absorption solvent to be recycled to the reaction step and/or the distillation step(s) (the first distillation step (3) and/or the second distillation column (6)). Moreover, a valuable resource (a useful component) may be recovered from the off-gas by using a membrane separation apparatus having a ceramic membrane represented by a zeolite membrane, a polymer membrane represented by a polyimide or a polyamide, or other membranes to be recycled to the reactor (1) and/or the distillation column(s) (the first distillation column (3) and/or the second distillation column (6)). The off-gas or the useful component may be fed to the second distillation step (6) directly or indirectly (for example, indirectly via a decanter) through at least one condenser (one or more condensers) for cooling and condensing the first overhead.

The concentration of acetaldehyde (AD) in the off-gas is lower than that of the condensate of the second overhead from the second distillation column (6). Thus, even if the off-gas is discharged to the outside of the system, the acetaldehyde removal efficiency (AD removal efficiency) could not be decreased. The useful component is effectively utilizable in the reaction system by recovering the valuable resource (the useful component such as DME) from the off-gas using the scrubbing apparatus and/or the membrane separation apparatus, and recycling the valuable resource to the reaction system (for example, a component such as DME is utilizable as a raw material of acetic acid). This process prevents the loss of the useful component.

At least a first portion of the raffinate formed in the extraction step (7) may be recycled to at least the reactor, a second portion of the raffinate may be recycled to the distillation column(s) of the distillation step(s) (the first distillation step (3) and/or the second distillation step (6)). In the extraction step (7), the second overhead may be subjected to water extraction stepwise (or batch-wise) or continuously with two or more theoretical stages. Further, the process may further comprise (8) a fourth distillation step for distilling the extract to form a fourth overhead containing an aldehyde and a bottom or lower aqueous stream. The aqueous stream may be reused for extraction in the extraction step (7).

Furthermore, the process stream having a reduced concentration of acetaldehyde formed by the separation step (a process stream obtained by removing acetaldehyde from the volatile phase and/or the succeeding process stream) may be recycled to the reactor. By such a recycling step, the acetaldehyde concentration in the reaction medium in the reactor may be maintained at not more than 400 ppm by weight. Further, by distilling the crude acetic acid stream to separate the crude acetic acid stream into a purified acetic acid, and a lower boiling point component and/or a higher boiling point component, at least one of the following (i) to (iii) may be satisfied: (i) the potassium permanganate test value of the purified acetic acid is maintained at not less than 120 minutes, (ii) the propionic acid concentration of the purified acetic acid is maintained at not more than 200 ppm by weight, and (iii) the iodide concentration of the purified acetic acid is maintained at not more than 100 ppb.

Another aspect of the present invention provides a process for separating at least one permanganate reducing compound (PRC) from a mixture containing water, acetic acid, methyl iodide, methyl acetate, dimethyl ether, methanol, at least one $C_{2-12}$alkyl iodide, and at least one PRC. In the process, (6) the mixture (the first overhead or a condensate thereof) is distilled while controlling the internal pressure of the distillation column to form a second overhead rich in acetaldehyde as a PRC, and methyl iodide; and (7) the second overhead is subjected to extraction with water to form an extract and a raffinate.

In the separation process, at least a portion of the raffinate may be recycled to the reaction step and/or the second distillation step. The recycled raffinate may be distilled together with the mixture.

The second overhead may be condensed to form a condensate and an off-gas, and the condensate may be subjected to the extraction step (7); (10) at least one component separated from the off-gas and selected from the group consisting of methyl iodide, methyl acetate, dimethyl ether, water, and carbon monoxide may be directly or indirectly recycled to the reaction step and the distillation step(s) (the first distillation step (3) and/or the second distillation step (6)).

The mixture may be a condensate of the first overhead (or an upper phase and/or a lower phase of a condensate). For example, the mixture may be a condensate obtainable by subjecting the reaction mixture (1) of methanol carbonylation to flash evaporation to form a volatile phase (2), distilling the volatile phase to form a first overhead (3), and condensing the first overhead. As the mixture, an upper phase and/or a lower phase of the condensate may be used.

A further aspect of the present invention also discloses a production apparatus corresponding to the process for producing acetic acid.

As used herein, the term "process unit" means an apparatus or a unit for operating a unit process, such as a reaction, an evaporation, a distillation, a cooling and/or condensation, a liquid-liquid separation, a holding (storage), an absorption, an extraction, an adsorption and/or ion exchange. As used herein, acetaldehyde and acetaldehyde-derived by-products that shorten a permanganate time in a potassium permanganate test may simply be referred to as PRC's. Examples of such a component of PRC's may include an aldehyde compound, and an alkyl iodide with two or more carbon atoms. Unless otherwise specifically noted, an acetaldehyde-containing aqueous phase obtainable by liquid-liquid (or biphasic) separation means is synonymous with a light phase or an upper phase, and a methyl iodide-containing organic phase obtainable by liquid-liquid (or biphasic) separation is synonymous with a heavy phase, a methyl iodide phase, or a lower phase. An aqueous phase obtainable by extraction means is synonymous with an extract, and an organic phase obtainable by extraction is synonymous with a raffinate.

Advantageous Effects of Invention

According to the present invention, the pressure of the distillation column is controllable, and the acetic acid production process is stably and safely operable without increasing the pressure of the distillation column. Further, it is not necessary to recycle a process stream in which acetaldehyde is concentrated to the reactor, and an improved acetaldehyde removal efficiency is achievable. Furthermore, the useful component(s) (e.g., DME) contained in the off-gas from the top of the column is recycled to the reactor to be utilizable as raw materials of acetic acid.

BRIEF DESCRIPTION OF DRAWINGS

FIG. 1 is a flowchart (or a flow diagram) for explaining a production process of acetic acid in accordance with an embodiment of the present invention.

DESCRIPTION OF EMBODIMENTS

Hereinafter, the present invention will be explained in detail with reference to the drawings if necessary. In the drawings and the description, each step and a main apparatus or unit for the corresponding step may be indicated by the same reference numeral.

The process (or apparatus) for continuously producing acetic acid as shown in the drawings comprises the steps: (1) a step for carbonylating methanol (a reaction system or a reactor); (2) a flash step for separating the reaction mixture into a volatile phase and a less-volatile phase (a flash evaporation step or flasher); (3) a first distillation step for separating the volatile phase into a first overhead and a crude acetic acid stream (a first distillation column or a splitter column), wherein the first overhead is rich in at least one lower boiling point component selected from methyl iodide and acetaldehyde, and the crude acetic acid stream is rich in acetic acid; and (4) a step for separating at least acetaldehyde from the first overhead. The separation step (4) comprises the steps: (5) a step for condensing the first overhead to form a condensate (or a biphasic separation step); (6) a second distillation step for distilling at least a portion of the condensate while controlling the internal pressure of the distillation column; (7) a step for extracting acetaldehyde from a second overhead to form an extract rich in acetaldehyde and a raffinate rich in methyl iodide; and (10) a step for recovering a useful component from an off-gas to recycle the useful component to the reactor directly or indirectly (not shown or depicted).

The process of the present invention has at least the steps (1) to (3), the second distillation step (6) and the extraction step (7) of the separation step (4), among these steps. Hereinafter, each step will be explained in detail.

(1) Reaction Step (Reactor)

In the reaction step (reactor) (1), methanol and carbon monoxide are continuously fed to a reactor for carbonylating methanol in the presence of a reaction medium containing a carbonylation catalyst system and water to produce acetic acid. Inside the reactor (1), a carbonylation reaction of methanol proceeds with forming an equilibrium between a liquid-phase reaction system and a gaseous-phase system. The liquid-phase reaction system contains reactant(s) and metal catalyst component(s), and the gaseous-phase system comprises carbon monoxide, by-products (hydrogen, methane, carbon dioxide) and a vaporized lower boiling point component or fraction (e.g., methyl iodide, acetic acid as a product, and methyl acetate). From the reactor (1), a reaction mixture is continuously introduced or fed to one or more flashers (catalyst separation columns or flash evaporators) (2), and a gas fraction (gaseous phase) is withdrawn via a line 12. The withdrawn gas fraction is cooled in a heat exchanger (condenser) C1 for condensation to form a condensate and a noncondensable gas. The condensate is returned to the reactor (1) via a line 13, and the noncondensable gas is fed to a scrubber unit having an absorption treatment unit (not shown) via a line 14. Returning the condensate to the reactor (1) allows part of the reaction heat to be removed. Incidentally, part of the reaction heat may be removed by returning the noncondensable gas to the reactor (1). A useful component (such as carbon monoxide and/or hydrogen, methyl iodide, or methyl acetate) recovered from the noncondensable gas by the scrubber unit may be recycled to the reactor (1).

The carbonylation catalyst system usually contains a metal catalyst (such as a cobalt catalyst, a rhodium catalyst, or an iridium catalyst), a catalyst stabilizer or reaction accelerator, and a co-catalyst. The metal catalysts may be used alone or in combination. The metal catalyst may preferably include a rhodium catalyst and an iridium catalyst (in particular, a rhodium catalyst).

The metal catalyst may be used in the form of a simple metal, a metal oxide (including a complex metal oxide), a metal hydroxide, a metal iodide, a metal carboxylate (e.g., an acetate), a metal salt of an inorganic acid (e.g., a sulfate, a nitrate, and a phosphate), or a metal complex. It is preferred to use the metal catalyst in a form (e.g., a complex form) dissolvable in a liquid phase (or a reaction liquid). The rhodium catalyst may preferably include, for example, a rhodium iodide complex {e.g., $RhI_3$, $RhI_2(CO)_4]^-$, and $[Rh(CO)_2I_2]^-$} and a rhodium carbonyl complex. The metal catalyst has a concentration of, for example, about 100 to 5000 ppm (on the basis of weight, the same applies hereinafter), preferably about 200 to 3000 ppm, more preferably about 300 to 2000 ppm, and particularly about 500 to 1500 ppm in the whole liquid phase in the reactor.

The catalyst stabilizer or reaction accelerator may include a metal iodide capable of producing an iodide ion in the reaction medium, for example, such as an alkali metal iodide (e.g., lithium iodide, sodium iodide, and potassium iodide). Among these stabilizers, lithium iodide is preferred. These co-catalysts or accelerators may be used alone or in combination. The catalyst stabilizer or reaction accelerator in the whole liquid phase in the reactor has a concentration of, for example, about 1 to 25% by weight, preferably about 2 to 22% by weight, and more preferably about 3 to 20% by weight. The iodide ion in the reaction system may have a concentration of, for example, about 0.05 to 2.5 mol/L and preferably about 0.25 to 1.5 mol/L.

As the co-catalyst, methyl iodide may be used. The methyl iodide in the whole liquid phase in the reactor has a concentration of, for example, about 1 to 30% by weight, preferably about 5 to 25% by weight, and more preferably about 6 to 20% by weight (e.g., about 8 to 18% by weight).

A preferred carbonylation catalyst system may comprise a rhodium catalyst, a metal iodide as a catalyst stabilizer (e.g., lithium iodide), and methyl iodide as a co-catalyst. To the reactor may be fed a catalyst mixture (a catalyst liquid) containing the carbonylation catalyst system and water.

The reaction medium (or liquid phase) usually contains product acetic acid, methyl acetate formed by a reaction of product acetic acid and raw material methanol, and water. The acetic acid also plays as a solvent. Moreover, the reaction medium (or the liquid phase) usually contains unreacted raw material methanol. The proportion of methyl acetate in the whole reaction liquid may be about 0.1 to 30% by weight, preferably about 0.3 to 20% by weight, and more preferably about 0.5 to 10% by weight (e.g., about 0.5 to 6% by weight). The water in the reaction medium may have a low concentration. The water in the whole reaction liquid has a concentration of, for example, about 0.1 to 15% by weight, preferably about 0.5 to 10% by weight, and more preferably about 0.8 to 5% by weight (e.g., about 1 to 3% by weight) and may usually be about 1 to 10% by weight (e.g., about 2 to 5% by weight). The concentration of acetic acid in the whole liquid phase may be, for example, about 30 to 90% by weight (e.g., about 35 to 85% by weight) and preferably about 45 to 80% by weight.

The carbon monoxide partial pressure in the reactor may be a pressure of, for example, about 0.2 to 3 MPa and preferably about 0.4 to 1.5 MPa in terms of absolute pressure. The carbonylation reaction produces hydrogen by a reaction of carbon monoxide with water. Hydrogen increases the catalyst activity. Thus hydrogen may be fed to the reactor if necessary. The hydrogen partial pressure in the reaction system may be a pressure of, for example, about 0.0005 to 0.25 MPa (e.g., about 0.001 to 0.2 MPa), preferably about 0.005 to 0.15 MPa, and more preferably about 0.01 to 0.12 MPa in terms of absolute pressure. From an off-gas produced in any step following the reaction step, a gas fraction (including hydrogen, carbon monoxide, or other components) may be recovered for recycling carbon monoxide and/or hydrogen to the reaction system, or a useful condensable component may be recovered for recycling the useful component to the reaction system.

The temperature of the carbonylation reaction may be, for example, about 150 to 250° C., preferably about 160 to 230° C., and more preferably about 170 to 220° C. The reaction pressure (total reactor pressure), including partial pressures of by-products, may be, for example, about 1.5 to 4 MPa in terms of gauge pressure.

The space time yield of the objective acetic acid in the reaction system may be, for example, about 5 mol/Lh to 50 mol/Lh, preferably about 8 mol/Lh to 40 mol/Lh, and more preferably about 10 mol/Lh to 30 mol/Lh.

The reaction mixture (the crude reaction liquid) contains acetic acid, lower boiling point components or impurities, each having a boiling point lower than acetic acid (e.g., methyl iodide as a co-catalyst, methyl acetate, water, and acetaldehyde as a by-product), and higher boiling point components or impurities, each having a boiling point higher than acetic acid [e.g., a metal catalyst component (e.g., a rhodium catalyst), lithium iodide as a catalyst stabilizer, and a $C_{3-12}$alkanecarboxylic acid (e.g., propionic acid)]. Further, by-products derived from acetaldehyde (acetaldehyde derivatives) are also produced. The acetaldehyde derivatives may include, for example, an aldehyde such as butyraldehyde, crotonaldehyde, 2-ethylcrotonaldehyde, and 2-ethylbutyraldehyde; a ketone such as acetone or methyl ethyl ketone; an aldol condensation product thereof; and a $C_{2-12}$alkyl iodide such as ethyl iodide, propyl iodide, butyl iodide, pentyl iodide, or hexyl iodide. The by-products may also include a 3-hydroxyalkanal (e.g., 3-hydroxybutanal); formic acid or the $C_{3-12}$alkanecarboxylic acid (such as propionic acid, butanoic acid, hexanoic acid, heptanoic acid, or octanoic acid); a $C_{3-12}$alkyl alcohol such as butyl alcohol or 2-ethylbutyl alcohol; an ester of methanol or the above alkyl alcohol with acetic acid or the above carboxylic acid; an ether of methanol and/or the above alkyl alcohol (a dialkyl ether such as dimethyl ether); and methane and a hydrocarbon with two or more carbon atoms (e.g., a $C_{2-12}$alkane).

These by-products are usually increased in proportion to the square to the cube of the concentration of acetaldehyde.

Acetaldehyde and the by-products derived from acetaldehyde (for example, other aldehydes, the ketone, and the aldol condensation product) belong to permanganate reducing compounds (PRC's). Thus, it is preferred to separate and remove acetaldehyde, which is a main by-product, and PRC's from the reaction mixture and/or the process stream(s) and to recover useful components (e.g., methyl iodide) from the process stream(s) for effective utilization. As used herein and in claims, methyl iodide is excluded from the PRC's, although the $C_{2-12}$alkyl iodide, including methyl iodide, also belongs to the PRC's.

According to one embodiment of the present invention, acetaldehyde is efficiently separable and removable and, even in a continuous reaction, recycling a process stream having little or no acetaldehyde to the reaction system allows reduction of the concentration of acetaldehyde in the reactor. With the decrease in acetaldehyde concentration or the elimination of acetaldehyde, the formation of by-products derived from acetaldehyde is significantly prevented. For example, the liquid phase in the reactor may have an acetaldehyde concentration of not more than 400 ppm (e.g., 0 or detection limit to 300 ppm) and preferably about 10 to 250 ppm (e.g., about 20 to 200 ppm). The alkyl iodide having 2 or more carbon atoms (such as hexyl iodide) may have a concentration of, for example, about 0.1 ppb to 1 ppm (e.g., about 0.5 to 500 ppb) and preferably about 1 to 100 ppb. The dimethyl ether (DME) may have a concentration of, for example, about 0.1 to 1000 ppm, preferably about 1 to 500 ppm (e.g., about 2 to 300 ppm), and more preferably about 3 to 200 ppm (e.g., about 5 to 100 ppm).

The reaction system is an exothermic reaction system that accompanies heat generation, and the reaction temperature may be controlled (or regulated) by installation of a heat-removable (or heat-removing) unit or a cooling unit (e.g., a jacket).

(2) Flash Evaporation Step

In the flash evaporation step (2), the reaction mixture which is continuously fed from the reactor (1) to a flasher (flash evaporator) (2) via a line 11 is flash-evaporated to form a volatile phase (2A) and a less-volatile phase (2B); the volatile phase (2A) contains product acetic acid, methyl iodide, acetaldehyde, methyl acetate, water, or other compounds, and the less-volatile phase (2B) contains the rhodium catalyst and lithium iodide. The less-volatile phase (2B) is cooled by a cooler C3, and the cooled product is recycled to the reactor of the reaction step (1) via a recycle line 21 to remove part of the reaction heat. At least a first portion of the volatile phase (2A) is fed to a distillation column of a first distillation step (3) via a line 22. In this embodiment, a second portion of the volatile phase (2A) is cooled and condensed in a condenser C2 on a line 23 to form a condensate and a noncondensable gas. The condensate is fed to a hold tank 25 through a line 24 and held in the hold tank 25, and is recycled to the reaction step (reactor) (1) via a line 26. The noncondensable gas is fed to a scrubber unit having an absorption treatment unit (not shown) via a line 27.

In another embodiment, a second portion of the volatile phase (2A) may be cooled and condensed in the condenser C2, and the cooled product (condensate and/or noncondensable fraction) in the condenser C2 may be fed to the liquid-liquid separation step (5) via a line (not shown) and may be held in a decanter (5) together with an overhead (3A) from the first distillation step (splitter column) (3), and a mixture of the cooled product and the overhead (3A) may be separated into two phases in the decanter (5). The second portion of the volatile phase (2A) may be fed, without condensation, to the second distillation step (6) directly or indirectly via the liquid-liquid separation step (5), or may be cooled and condensed in one or a plurality of condensers C2 to form two phases (an aqueous phase or an organic phase) for subjecting the aqueous phase or the organic phase (at least the aqueous phase) to the second distillation step (6) directly or indirectly via the liquid-liquid separation step (5). For example, the second portion of the volatile phase (2A) may optionally be condensed as described above (and optionally be liquid-liquid separated) and mix with the condensate obtained in the liquid-liquid separation step (5), and the mixture may be subjected to the second distillation step (6).

If necessary, the catalyst component (metal catalyst component) may be separated from the less-volatile phase (2B) by one or more separation steps and may be recycled to the reaction step (1).

The flash evaporation may include a thermostatic flash in which the reaction mixture is heated and depressurized, an adiabatic flash in which the reaction mixture is depressurized without heating, or a combination of these flash conditions. By such a flash evaporation, the reaction mixture may be separated into the vapor phase and the liquid phase. For example, the flash evaporation may be carried out at a temperature of the reaction mixture of about 80 to 250° C. and preferably about 120 to 180° C., and a pressure (gauge pressure) of the reaction mixture of about 0.01 to 1 MPa, preferably about 0.05 to 0.5 MPa, and more preferably about 0.1 to 0.2 MPa.

(3) First Distillation Step (Splitter Column or Distillation Column)

In the first distillation step (splitter column) (3), the volatile phase (2A) is separated into a first overhead (3A), an acetic acid stream (3B), and a bottom stream (3C); the first overhead (3A) (overhead gas, lower boiling point stream or lower boiling point component or fraction) is withdrawn from a top or upper part of the column via a withdrawing line 33, the acetic acid stream (3B) is side-cut as a side-withdrawing stream via a line 36 and mainly contains acetic acid, and the bottom stream (3C) (higher boiling point stream or higher boiling point component or fraction) is withdrawn from a bottom or lower part of the column via a bottom line 31.

The first overhead stream (3A), which corresponds to a mixture (3A), contains at least one permanganate reducing compound (PRC) and methyl iodide. The PRC contains at least by-product acetaldehyde. The first overhead (3A) usually contains methyl acetate and practically further contains acetic acid, water, dimethyl ether, by-products derived from acetaldehyde (for example, an acetaldehyde derivative, e.g., an aldehyde such as crotonaldehyde or butyraldehyde, a $C_{2-12}$alkyl iodide and a $C_{3-12}$alkanecarboxylic acid; and a $C_{2-12}$alkane). The first overhead (3A) also usually contains methanol.

The acetic acid stream or side-cut stream (3B) is further fed to a purification step by a distillation column or other means (not shown) to remove water and/or higher boiling point impurities or other impurities from the stream (3B) for producing purified acetic acid with a high purity. The purification step may have an ion exchange unit at the downstream side of the distillation column in order to remove an iodine component (such as hydrogen iodide or an alkyl iodide). The liquid stream (3C) usually contains at least water and acetic acid and also practically contains methanol, methyl iodide, methyl acetate, propionic acid, or other compounds. The liquid stream (3C) may contain an entrained metal catalyst component. For that reason, a portion of the liquid stream (3C) may be recycled to the flasher (flash evaporator) (2) via the line 32, or a portion or whole of the liquid stream (3C) may be recycled to the reaction step (reactor) (1) via a line 31 and a line 100. A portion or whole of the liquid stream (3C) may be discharged via the line 31.

As the distillation column (splitter column) (3), there may be used a plate column, a packed column, or other columns. The internal temperature of the distillation column (splitter column) depends on an internal pressure thereof. At the internal pressure of an atmospheric pressure (1 atm=about 0.1 MPa), the distillation column may have a column top temperature of, for example, about 50 to 180° C. and preferably about 80 to 160° C., or may have a column bottom temperature of, for example, about 60 to 200° C. and preferably about 100 to 160° C. The distillation column may have a pressure (gauge pressure) of, for example, about 0.05 to 0.5 MPa, preferably about 0.08 to 0.4 MPa, and more preferably about 0.1 to 0.3 MPa.

The distillation column may have a theoretical stage (or a theoretical stage number) of, for example, about 2 to 100 and preferably about 8 to 30. The reflux ratio of the distillation column may be infinity (wherein the infinity means that all the condensate from the top of the distillation column is recycled to the top of the distillation column) or may be, for example, about 1 to 1000 and preferably about 10 to 100.

In the first distillation step (3), the volatile phase (2A) is distilled to separate the volatile phase into the first overhead (3A) and the side-cut crude acetic acid stream (3B); the first overhead (3A) is rich in at least one lower boiling point component selected from methyl iodide and acetaldehyde, and the crude acetic acid stream (3B) is rich in acetic acid. It is not essential to separate a stream as the bottom liquid stream (3C) from the volatile phase.

The liquid stream (3C) may be discharged. A portion or whole of the liquid stream (3C) may be returned to the splitter column (2) or may be recycled to the reactor of the reaction step (1).

The first overhead (3A) may be subjected, as a mixture (3A) in a gaseous form or phase, to the second distillation step (6) without passing through the condensation and liquid-liquid separation step (5), or the first overhead (3A) may be condensed and the resulting condensate may be subjected to the second distillation step (6) without liquid-liquid separation. In a preferred embodiment, in order to extract PRC's effectively, the first overhead (3A) is subjected to the liquid-liquid separation step (5) of the separation step (4) described later to form a mixture (3A) in which methyl iodide, in particularly, both methyl iodide and PRC's, are concentrated. Specifically, the mixture (3A) may be any one of the first overhead (3A), the condensate of the first overhead (3A), and an upper phase and/or a lower phase formed by liquid-liquid separation of the condensate. The mixture (3A) usually contains water, acetic acid, methyl iodide, methyl acetate, dimethyl ether, at least one $C_{2-12}$alkyl iodide, and at least one permanganate reducing compound (PRC), and also usually contains methanol. A preferred mixture (3A) includes the condensate, particularly, the upper phase and/or the lower phase (or a mixture of the upper phase and the lower phase) formed by liquid-liquid separation. Specifically, in the upper phase (aqueous phase), acetaldehyde is concentrated; the lower phase (organic phase) also contains acetaldehyde, and in the lower phase, dimethyl ether, which has a high vapor pressure and a high affinity or miscibility with water or methyl iodide, is concentrated. Accordingly, even if the upper phase, the lower phase, or the mixture of the upper phase and the lower phase as the mixture (3A) is distilled in the second distillation step (2), the process of the present invention prevents an excessively high internal pressure of the distillation column.

(4) Separation Step

As described above, the first overhead (3A) contains impurities such as PRC's and useful components such as methyl iodide, methyl acetate, dimethyl ether, and methanol. Thus, in the separation step (4), at least acetaldehyde is separated from the first overhead (3A). In particular, the first overhead (3A) is separated into a stream rich in acetaldehyde and a stream rich in useful methyl iodide.

The separation step (4) comprises the steps: (5) a liquid-liquid separation step for condensing the first overhead (3A) to form a condensate (condensation step) and biphasically separating the condensate into an upper aqueous phase and a lower organic phase (phase-separation step) (a step for forming a condensate or an upper phase and/or a lower phase as a mixture); (6) a second distillation step for distilling at least a portion of the condensate (the upper phase and/or the lower phase formed by liquid-liquid separation) while controlling the internal pressure of the distillation column to form a second overhead rich in acetaldehyde and methyl iodide and a bottom or lower stream (an aldehyde separation step); and (7) a step for extracting acetaldehyde from the second overhead formed in the step (6) to form an extract rich in acetaldehyde and a raffinate rich in methyl iodide (an extraction step). The separation step (4) may further comprise (8) a fourth distillation step for distilling the extract to form a fourth overhead containing an aldehyde, and a bottom or lower aqueous stream (an aldehyde separation step, not shown in the drawing).

(5) Liquid-Liquid Separation Step

The liquid-liquid separation step (5) comprises the steps: (11a) a condensation step for cooling and condensing the first overhead (3A) fed via the line 33 in a heat exchanger (condenser) C4 to form a condensate and a noncondensable gas, wherein the condensate is rich in methyl iodide and contains water, methyl acetate, or other compounds; and (11b) a biphasic separation step for separating the condensate into an upper phase (an aqueous phase) rich in acetaldehyde and a lower phase (an organic phase) rich in methyl iodide in the liquid-liquid separation step (decanter) (5). The upper phase (the aqueous phase) and/or the lower phase (the organic phase) is subjected to the second distillation step (6). The aqueous phase is an upper phase or light phase being rich in acetaldehyde and containing methyl acetate, acetic acid, methyl iodide, or other compounds. The lower phase is an organic phase or heavy phase being rich in methyl iodide and containing methyl acetate, acetic acid, water, or other compounds. The noncondensable gas, which is formed in the heat exchanger (condenser) C4 of the condensation step, is rich in methyl iodide and contains methyl acetate, carbon monoxide, or other compounds. Thus the noncondensable gas may be fed to a scrubber unit having an absorption treatment unit (not shown) via a line 35.

In this embodiment, a portion of the condensate (the upper phase in the decanter (5) in this embodiment) is returned to the first distillation column (splitter column) (3) for reflux via a reflux line 42, and a portion of the lower phase (the organic phase or heavy phase rich in methyl iodide) is recycled to the reactor (1) via lines 41 and 100. Incidentally, a portion of the upper phase (the aqueous phase or light phase rich in acetaldehyde) in the decanter (5) may also be recycled to the reactor (1).

In a case where the first overhead stream (3A) is cooled stepwise in a plurality of condensers (a plurality of condensers successively lower in cooling temperature) to form a plurality of condensates successively lower in temperature, a condensate formed by a subsequent condenser has a higher concentration of acetaldehyde compared with a process liquid (a condensate) formed by a first condenser. Accordingly, a condensate having a high concentration of acetaldehyde may be fed to the second distillation step (6) for separating acetaldehyde from the condensate.

Furthermore, the plural condensers allows effective utilization of useful components in an off-gas. Specifically, a plurality of condensers C4, being sequentially lower in cooling temperature with more downstream direction, is disposed on the line 33, and the off-gas is introduced upstream of the condensers C4 or between the condensers C4 and is cooled. This serial condensation manner enables separation of the off-gas into a condensate and a noncondensable gas without separation of the off-gas by a scrubber unit or other means. The useful components are effectively utilizable for the reaction and an aldehyde is effectively separated by treating the noncondensable gas with a scrubbing apparatus (a scrubber unit), recycling a first portion of the condensate to the reaction step (1), and recycling a second portion of the condensate to the second distillation step (6).

The off-gas is any off-gas produced in the process for producing acetic acid. For example, the off-gas may include an off-gas 14 from the reactor (1), an off-gas 27 from the flasher (2), off-gases 60, 71 from the after-mentioned second distillation step (6), an off-gas from the liquid-liquid separation step (5), an off-gas from the after-mentioned extraction step (7) (for example, an off-gas of an extractive distillation step), an off-gas from the after-mentioned fourth distillation step, or other off-gases. As the off-gas, at least the off-gas from the second distillation step (6) is used practically. The condensate is recycled to at least one unit selected from the reactor (1) and the distillation column(s) (the first distillation column (3) and/or the second distillation column (6)) of the distillation step. The condensate is usually recycled to both reactor (1) and second distillation column (6).

If necessary, in addition to the liquid-liquid separation step (decanter (5)) for biphasically separating the condensate, a buffer tank or hold tank for temporarily holding (or retaining) the condensate (the separated lower phase or upper phase) in the decanter (5) may be utilized for suppressing the flow rate fluctuation of the process stream.

At least one phase of the upper phase (aqueous phase or light phase) rich in acetaldehyde and the lower phase (organic phase or heavy phase) rich in methyl iodide formed in the decanter (5) may be fed to the second distillation step (aldehyde separation step) (6) and/or the reaction step (1). For example, to the second distillation step (aldehyde separation step) (6), the upper phase (aqueous phase or light phase) may be fed instead of the lower phase (organic phase or heavy phase). To the reaction step (1), the lower phase (organic phase or heavy phase) may be recycled instead of the upper phase (aqueous phase or light phase), or both of the upper phase and the lower phase may be recycled.

(6) Second Distillation Step (Aldehyde Separation Step)

The condensate formed in the liquid-liquid separation step (5) is fed to a second distillation step or distillation column (6). In the second distillation column (6), the condensate is distilled to form a second overhead(s) (5A) (6A) being rich in methyl iodide and PRC acetaldehyde and a bottom stream(s) (5B) (6B) being rich in methyl iodide and containing methyl acetate.

In this embodiment, at least a portion of the aqueous phase or light phase (which is rich in acetaldehyde) and/or at least a portion of the organic phase or heavy phase (which is rich in methyl iodide and contains methyl acetate or other compounds) in the condensate formed in the liquid-liquid separation step (5) is fed to the second distillation step or distillation column (6). More specifically, a first portion of the acetaldehyde-rich aqueous phase or light phase formed in the step (5) is fed to the second distillation step or distillation column (6) via a line 43, and a second portion of the aqueous phase is recycled to the reactor (1) via a line 44. At least a portion of the organic phase or heavy phase being rich in methyl iodide and containing methyl acetate or other compounds is fed to the second distillation step or distillation column (6) via a line 45. In the second distillation step (6), at least a portion of at least one phase of the aqueous phase and the organic phase is distilled. At least a portion of the aqueous phase, or at least a portion of the organic phase may be distilled, or at least a portion of both aqueous and organic phases may be distilled.

The second distillation step (6) comprises at least one distillation column. In this embodiment, the second distillation step (6) comprises a plurality of distillation columns (in this embodiment, two distillation columns (6a) and (6b)). Specifically, the condensate fed to the second distillation column (6a) via lines 43, 45 (in this embodiment, at least a portion of at least one phase of the aqueous and the organic phases) is distilled to form an overhead (5A) from an overhead withdrawing line 55 and a bottom stream (5B) from a bottom line 51. The bottom stream (5B) is rich in methyl iodide and contains methyl acetate, acetic acid, water, or other compounds. The overhead (5A), which is rich in methyl iodide and acetaldehyde, is cooled and condensed in a condenser C5 on the line 55 to form a condensate and a noncondensable gas. The condensate, which is rich in methyl iodide and acetaldehyde, is fed to a hold tank 57 through a line 56 and is held in the hold tank 57. A first portion of the condensate is returned to the second distillation column (6a) for reflux via a reflux line 58, and a second portion of the condensate is fed to a third distillation column (6b) via line (59). The noncondensable gas (containing methyl iodide or other compounds), which has not been condensed in the condenser C5, is fed to a scrubber unit having an absorption treatment unit (not shown) via a line 60.

In the third distillation column (6b), the condensate is distilled to form an overhead (6A) from a line 62 and a bottom stream (6B) from a line 61. The bottom stream (6B) is rich in methyl iodide and contains methyl acetate or other compounds. The overhead (6A) is cooled and condensed in a condenser C6 on the line 62 to form a condensate and a noncondensable gas. The condensate is fed to a hold tank 65 through a line 64 and is held in the hold tank 65. A first portion of the condensate is returned to the third distillation column (6b) for reflux via a reflux line 66, and a second portion of the condensate, which is rich in methyl iodide and acetaldehyde, is fed to the extraction step (7). The noncondensable gas, which has not been condensed in the condenser C6, may be fed to a scrubber unit having an absorption treatment unit and/or a membrane separation apparatus (membrane separation unit) (not shown) via lines 69, 71. Furthermore, in place of the scrubber unit and/or the membrane separation unit, or in addition to the scrubber unit and/or the membrane separation unit, a plurality of condensers C4 sequentially lower in cooling temperature may be disposed as described above. The noncondensable gas 71 may be introduced directly (or as it is) upstream of the plurality of condensers or between the plurality of condensers to recover useful components. The useful components may be recycled to the reaction step and/or the distillation step for effective utilization. The noncondensable gas 71 may be recycled to the reaction step (1) and/or the distillation step via at least one condenser C4 and a line including a recycle line. The distillation step may be at least one of the first distillation step (3) and the second distillation step (6). For example, the noncondensable gas 71 may directly be recycled to the second distillation step (6) via the condenser C4 of the first distillation step (3) and a line including a recycle line, or may indirectly recycled to the second distillation step (6) via the decanter (5). In the second distillation step (6), the noncondensable gas 71 may be recycled to the second distillation column (6a) and/or the third distillation column (6b).

A first portion of the bottom stream (5B) from the second distillation column (6a) may be recycled to the reactor (1) via lines 52, 100. A second portion of the bottom stream (5B) may be fed to the decanter (5) via a line 53 branched from the line 51. Furthermore, a third portion of the bottom stream (5B) may be returned to the third distillation column (6b) for reflux via a line 54 branched from the line 51 and a reflux line 66. The bottom stream (6B) from the third distillation column (6b) may be recycled to the reactor (1) via lines 61, 100.

In the second distillation step (6) (a plurality of distillation columns (6a) and (6b)), a lower boiling point by-product having a high vapor pressure, such as dimethyl ether, may be produced. Thus in the top of the third distillation column (6b), the lower boiling point component having a high vapor pressure (methyl iodide, acetaldehyde, dimethyl ether, and others) may gradually be concentrated (or the concentration of the lower boiling point component having a high vapor pressure may be increased) with the distillation to raise the pressure of the column.

According to one embodiment of the present invention, even in a case where a component which may cause an increased pressure is distilled in the column, the distillation is smoothly and safely operable without the increase in pressure. Specifically, a pressure control unit PC (68) is disposed at the top of the third distillation column (6b), and the internal pressure of the third distillation column (6b) (in this embodiment, the pressure of the overhead (6A) in the line 62) is detected by a pressure sensor. If the detected value is larger than a standard value (a standard value which may have a threshold value), the pressure control unit PC (68) provides a controlling signal of a controlling variable to a pressure control valve 70 (a valve 70 on a line 71) which is linked to the unit by a dotted line in FIG. 1, and the valve is opened and the noncondensable gas is discharged from the line 71 to maintain a predetermined pressure in the column. In contrast, if the detected value is smaller than the standard value, the pressure control unit PC (68) provides a controlling signal to the pressure control valve 70 to keep the valve close. That is, the pressure control unit controls the internal pressure of the third distillation column (6b) by regulating or controlling the outflow rate of the noncondensable gas (overhead). Moreover, if the detected value is excessively smaller than the standard value, nitrogen gas $N_2$ is introduced via a line 72 to maintain a predetermined pressure in the column. In order to improve the speed of response and/or control of the control valve 70, the control valve 70 may remain open at an appropriate degree of opening by feeding a small quantity of the nitrogen gas from the line 72 constantly. The flow rate (kg/H) of the nitrogen gas may be not more than 1% (e.g., about 0.0001 to 1%) and preferably not more than 0.1% (e.g., about 0.001 to 0.05%) relative to a flow rate at a line 59.

The second distillation step (aldehyde separation step) (6) does not necessarily comprise plural distillation columns, and may comprise a single distillation column. In the second distillation step (aldehyde separation step) (6), the mixture (3A), for example, the condensate, or the upper phase and/or the lower phase formed in the liquid-liquid separation step (5), is distilled. For example, because the acetaldehyde content of the upper phase is higher than that of the lower phase, the upper phase formed in the liquid-liquid separation step (5) may be distilled in place of the lower phase, or at least a portion of the upper phase (for example, at least a portion of the upper phase and at least a portion of the lower phase) may be distilled. The lower phase formed in the liquid-liquid separation step (5) is rich in methyl iodide and also contains dimethyl ether, methyl acetate, methanol, water, or other compounds. Thus the distillation of at least the lower phase in the second distillation step (aldehyde separation step) (6) may cause an increase in the internal pressure of the column. According to the present invention, the increase in the internal pressure of the column is effectively preventable as described above. Thus, according to the present invention, at least a portion (a portion or whole) of the lower phase (organic phase) may be distilled in the second distillation step (aldehyde separation step) (6).

In a case where the second distillation step (6) comprises a single distillation column, the first overhead is distilled while controlling the internal pressure of the distillation column. In a case where the second distillation step (6) comprises a plurality of distillation steps (continuous distillation step by a plurality of distillation columns), the first overhead or mixture (3A) may be distilled while controlling the internal pressure of at least one distillation column (distillation column(s) on the upstream, intermediate, and/or downstream sides). In a preferred embodiment, the first overhead may be distilled while controlling the internal pressure of a distillation column in which a lower boiling point component having a high vapor pressure is liable to concentrate, for example, at least a downstream side distillation column (a most downstream side distillation column).

For the pressure control of the distillation column, various industrially available methods may be used. As described above, the pressure may be controlled by regulating the outflow rate of the noncondensable gas (overhead). In a process using plural distillation columns, the pressure may be controlling by detecting the pressure and/or the flow rate at the withdrawing port communicating with a gaseous phase in the hold tank 65, which is disposed downstream of the condenser C6, and regulating the amount of the noncondensable gas (off-gas) accordingly. Further, a pressure sensor may be attached to the top of the distillation column to control the pressure. Furthermore, the pressure may be controlled in this embodiment as follows: the temperature and/or the flow rate of a cooling water for the condenser C6 is regulated to control the process temperature which results in the quantitative ratio of a noncondensable gas containing a component noncondensable and a produced condensate at the process temperature, and the gas amount discharged from the line 71 is regulated.

In a process containing a step for condensing the second overhead from the second distillation step or the second distillation column (6) to separate the second overhead into a condensate and an off-gas, the concentration of acetaldehyde (AD) in the off-gas is lower than that in the condensate. Thus, in such a process, even if the off-gas is discharged to the outside of the system, the acetaldehyde removal efficiency (AD removal efficiency) hardly decreases. Further, since the pressure control unit allows prevention of the flow rate and/or pressure fluctuation of the process stream, acetaldehyde is stably removable and the acetaldehyde removal efficiency is improvable.

In particular, in a case where the condensate is subjected to the extraction step (7), and (10) at least one component selected from the group consisting of methyl iodide, methyl acetate, dimethyl ether, water, and carbon monoxide is recovered from the off-gas to recycle the recovered component to the reaction step (1) and/or the distillation step (the first distillation step (3) and/or the second distillation step (6)) directly or indirectly, the useful component in the off-gas is effectively utilizable for the reaction without discharge. In addition, this process allows the improved removal efficiency of acetaldehyde and other PRC's.

As the distillation column of the second distillation step (6), there may be used a plate column, a packed column, or other columns. The internal temperature of the distillation column of the second distillation step (6) depends on an internal pressure thereof. At the internal pressure of an atmospheric pressure (1 atm=about 0.1 MPa), the distillation column may have a column top temperature of, for example, about 20 to 100° C. and preferably about 40 to 70° C., or may have a column bottom temperature of, for example, about 40 to 120° C. and preferably about 60 to 90° C. The distillation column of the second distillation step may have a pressure (gauge pressure) of, for example, about 0.01 to 0.6 MPa, preferably about 0.13 to 0.4 MPa, and about more preferably 0.15 to 0.35 MPa. A preferred pressure condition is selected depending on an advantageous cost with considering the separation efficiency, the amount of energy to be used, the cost of equipment or others. The distillation is operated so that the pressure value selected may be constant. The fluctuation of the operating pressure results in a change of the boiling point of a component to be separated by distillation, and thus a desired separation by distillation is adversely affected. As will be understood, the operation cannot be conducted at a pressure beyond the withstand pressure condition of equipment in view of safety.

The distillation column may have a theoretical stage (or a theoretical stage number) of, for example, about 10 to 150 and preferably about 20 to 90. The reflux ratio of the distillation column may be infinity or may be, for example, about 1 to 1000 and preferably about 50 to 400.

Incidentally, the gas to be introduced from the line 72 is not limited to nitrogen gas. For example, an off-gas form the above-described scrubber unit (a containing carbon monoxide, carbon dioxide, nitrogen gas, or other gases) or an inert gas or inactive gas (e.g., argon) may be introduced.

(7) Extraction Step

In the extraction step (7), the condensate from a line 67 is subjected to a water extraction in a water extraction unit (a water extractor) to biphasically separate the condensate into an organic phase (a raffinate) rich in methyl iodide and an aqueous phase (an extract) rich in acetaldehyde. In this embodiment, the extraction step (7) comprises two water extraction units (water extractors). Specifically, in a first water extraction unit (a water extractor) (8), the condensate (which may have been cooled) from the line 67 is subjected to extraction with water (e.g., a cooled water) supplied from a predetermined line (not shown), or the condensate is mixed with a cooled water, to form a first raffinate (7B) and a first extract (7A). In a second water extraction unit (a water extractor) (9), the first raffinate (7B) is subjected to extraction with water to form a second raffinate (8B) and a second extract (8A). Thus the second raffinate (8B) has a significantly reduced concentration of acetaldehyde, and a first portion of the second raffinate (8B) is recycled to the reactor (1) via lines 91, 92, 100, and a second portion of the second raffinate (8B) is recycled to the second distillation step (6) via aline 93. In this embodiment, the second portion of the second raffinate (8B) is fed to the distillation column (6b), which is a downstream column of second distillation step (aldehyde separation step) (6).

The first and second extracts (7A) (8A), which are rich in acetaldehyde, may be distilled in the succeeding distillation column (not shown) of the fourth distillation step (8) to recover water, or may be discharged or discarded without distillation.

At least a portion of the raffinate(s) may be recycled to the reaction step (1) and/or the distillation step (s) (the first distillation step (3) and/or the second distillation step (6)). Typically, at least a portion of the raffinate (s) can be recycled to the reaction step (1) and/or the distillation step (6). At least a portion of the raffinate (s) may be recycled to at least the reactor, or a portion of the raffinate(s) may be recycled to the distillation column of the second distillation step (6). In particular, at least a portion of the raffinate (s) may be recycled to the distillation column of the second distillation step (6) for distilling the recycled raffinate together with the mixture (3A). Incidentally, even in a case where the whole of the raffinate(s) is distilled together with the mixture (3A) in the distillation column of the second distillation step (6), the pressure control unit prevents the fluctuation of the internal pressure of the column. Thus this allows stable and safe operation. Further, in the process in which the second distillation step (aldehyde separation step) (6) comprises a plurality of distillation columns, a portion of the second raffinate (8B) may be fed to any distillation column, for example, the second distillation column (6a) and/or the third distillation column (6b). In a preferred embodiment, if the pressure of the distillation column may rise, a portion of the second raffinate (8B) may be fed to a distillation column provided with a pressure control unit, for example, a downstream distillation column.

In the extraction step (7), the second overhead(s) (5A) (6A) may be subjected to extraction with water intermittently (stepwise) or continuously. The water extraction may be performed by using one or more extractors. As each one of the extractors, there may, for example, be used a combination of a mixer with a settler, a combination of a static mixer with a decanter, a rotated disk contactor (RDC), a Karr column, a spray column, a packed column, a perforated plate column, a baffled column, and a pulse column. The extractor (extraction column) may be a single-stage extraction unit for extracting an object from a mixture of the object and water and separating the mixture into liquid phases, or may have a plurality of the single-stage extraction units arranged in a cascade manner. The water extraction may be carried out with theoretical two or more stages. For example, the extractor may be a multi-stage extraction unit that comprises a plurality of extractors (each extractor having a theoretical stage (or a theoretical number of plates) of 1) for sequential extraction. Moreover, the extractor may be a multi-stage extraction unit in which plural extractors have been installed in a single unit, for example, a single extraction unit having the theoretical stages equivalent to a multi-stage extraction unit (the theoretical stages corresponding to multi-stage extraction). Moreover, the extraction may be either a batch system or a continuous system, or may be performed in either a parallel extraction or a countercurrent extraction. The water extractor may have a theoretical stage (or a theoretical number of plates) of 1 or may have a theoretical stage of about 0.5 to 5. For the water extraction, water from the outside of the process may be used, or water in the process may be reused.

In the water extraction, the ratio of the flow rate (m³/hr) of the condensate relative to that of the water [the former/the latter] may be about 0.1/0.9 to 0.9/0.1 and preferably about 0.3/0.7 to 0.8/0.2.

The water extraction temperature may be about −10° C. to 70° C., preferably about 5 to 60° C., and more preferably about 10 to 50° C. The water extraction may be performed under an atmospheric pressure or an applied pressure, and may, for example, be performed at a gauge pressure of about 0.1 to 0.5 MPa and preferably about 0.15 to 0.4 MPa.

For the extraction step (7), a water extractive distillation column may be used instead of the water extraction unit (water extractor). In the water extractive distillation, the condensate is fed to the water extractive distillation column, and an extractant (water) is fed to an upper part of the distillation column to form a raffinate rich in methyl iodide as an overhead and a water extract (an extract containing acetaldehyde) as a bottom liquid.

As the water extractive distillation column, there may be used a plate column, a packed column, or other columns. The weight ratio of the flow rate of the extractant (water) relative to that of the condensate (in terms of liquid stream) [the former/the latter] may be selected from a range of about 0.1/100 to 10000/100 or may usually be about 25/100 to 2500/100 and preferably about 70/100 to 1500/100.

For the water extractive distillation, the extractant (water) may have a temperature of, for example, about 0 to 60° C., preferably about 10 to 50° C., and more preferably about 20 to 40° C. or may have an ordinary temperature (e.g., about 15 to 25° C.). The extractant (water) may be added to the distillation column after being heated or turned to vapor.

The internal temperature of the water extractive distillation column depends on an internal pressure thereof. At the internal pressure of an atmospheric pressure, the distillation column may have a column top temperature of, for example, about 10 to 120° C. and preferably about 20 to 90° C., or may have a column bottom temperature of, for example, about 15 to 150° C. and preferably about 25 to 120° C. The distillation column may have a column top pressure (absolute pressure) of, for example, about 0.1 to 0.5 MPa and preferably about 0.2 to 0.4 MPa.

The distillation column may have a theoretical stage of, for example, about 0.5 to 30 and preferably about 2 to 20. The reflux ratio in the distillation column may be, for example, about 0.01 to 500, preferably about 0.5 to 50, and more preferably about 2 to 20.

Thus, the extraction step (7) comprises the steps of: extracting the condensate of the second overhead with water by the water extractive distillation and/or the water extractor, feeding the extract to the fourth distillation step (8), and recycling the raffinate to the reaction step (1) and the distillation step (6).

The noncondensable gas (off-gas) from the extraction step (7), for example, the gas phases from the water extraction units (water extractors) (8) (9) or the noncondensable gas produced by the water extractive distillation may be introduced to a plurality of condensers, in place of a scrubber unit and/or a membrane separation unit or in addition to the scrubber unit and/or the membrane separation unit for recovering useful components, as described above. The useful components may be recycled to the reaction step and/or the distillation step(s) (the first distillation step (3) and/or the second distillation step (6)) for effective reutilization.

(8) Fourth Distillation Step (Aldehyde Separation Step)

In a distillation column of the fourth distillation step (8) (not shown), the extract formed in the extraction step (7) (in the above embodiment, the first and second extracts (7A) (8A)) is distilled to form a fourth overhead rich in acetaldehyde and a bottom stream (a lower stream) rich in water. The bottom stream (aqueous stream) is recycled as an extraction water (extractant) in the extraction step (7). The fourth overhead is cooled and condensed in one or more condensers to form a condensate and a noncondensable gas; the condensate contains water, methyl iodide, acetaldehyde, or other compounds, and the noncondensable gas contains acetaldehyde. The noncondensable gas may be fed to a scrubber unit having an absorption treatment unit (not shown). As described above, in place of a scrubber unit and/or a membrane separation unit, or in addition to the scrubber unit and/or the membrane separation unit, plural condensers C4 sequentially lower in cooling temperature may be disposed, and the noncondensable gas may be introduced as it is upstream of the plural condensers or between the plural condensers to recover useful components which may be utilized effectively for the reaction.

As the distillation column of the fourth distillation step (8), there may be used a plate column, a packed column, or other columns. The internal temperature of the distillation column of the fourth distillation step (8) depends on an internal pressure thereof. At the internal pressure of an atmospheric pressure (1 atm=about 0.1 MPa), the distillation column may have a column top temperature of, for example, about 20 to 150° C. and preferably about 50 to 120° C., or may have a column bottom temperature of, for example, about 40 to 180° C. and preferably about 80 to 160° C. The distillation column may have a pressure (gauge pressure) of, for example, about 0.0 to 0.5 MPa, preferably about 0.1 to 0.3 MPa, and more preferably about 0.12 to 0.25 MPa.

The distillation column may have a theoretical stage of, for example, about 1 to 30 and preferably about 2 to 10. The reflux ratio of the distillation column may be infinity or may be, for example, about 0.1 to 100 and preferably about 2 to 20.

(10) Off-Gas Treatment Step

Though the noncondensable gas (off-gas) produced from the above process may be discharged to the outside of the system, the noncondensable gas (off-gas) also contains useful components such as methyl iodide, methyl acetate, dimethyl ether, water, and carbon monoxide. Thus the noncondensable gas (off-gas) is preferably treated in the off-gas treatment step (10) to separate or recover useful components which are then directly or indirectly recycled to the reaction step (1) and/or the distillation step(s) (the first distillation step (3) and/or the second distillation step (6)) for effective utilization. For example, the noncondensable gas (off-gas) may be fed upstream of at least one condenser, in particular, a plurality of condensers being sequentially lower in condensation temperature with more downstream direction (for example, the plural condensers C4 disposed on the line 33 of the first overhead (3A)) or between the plural condensers, and cooled and condensed to form a condensation fraction (condensate) which may be recycled to the reaction step (1) and/or the distillation step(s) (the first distillation step (3) and/or the second distillation column (6)). Specifically, the noncondensable gas may be recycled to the reaction step (1) and/or the distillation step(s) (the first distillation step (3) and/or the second distillation column (6)) via at least one condenser. The noncondensable gas (off-gas) may be any noncondensable gas produced from the above process, for example, a noncondensable gas (an off-gas rich in carbon monoxide and methyl iodide) 14 from the reactor (1), a noncondensable gas (an off-gas rich in acetic acid, methyl iodide, and methyl acetate) 27 from the flasher (2), a noncondensable gas 35 which has not been condensed in the condenser C4 of the first distillation step (3) (and a nonliquefied component in the decanter (5)), and noncondensable gases (off-gases) 60, 71 from the second distillation step (6) (and optionally an off-gas from the extraction step (7)). The noncondensable gas usually contains at least the noncondensable gases (off-gases) 60, 71 from the second distillation step (6).

The noncondensable gas may be recycled directly to at least one distillation step of the first distillation step (3) and the second distillation step (6) via at least one condenser (one or more condensers) C4, or may be recycled indirectly to at least one distillation step of the first distillation step (3) and the second distillation step (6) (for example, may be recycled indirectly to the first distillation step (3) and/or the second distillation column (6*a*) via the decanter (5)). In the second distillation step (6), the noncondensable gas may be recycled to the second distillation column (6*a*) and/or the third distillation column (6*b*).

The noncondensable gas (off-gas) may be treated with a scrubber unit (or a scrubbing apparatus) having an absorption treatment unit. More specifically, the noncondensable gas (off-gas) may be absorbed to an absorption solvent in an absorption column under an applied pressure, and from the resulting absorption solvent, at least one component selected from the group consisting of methyl iodide, methyl acetate, dimethyl ether, water, and carbon monoxide may be stripped and recycled to the reaction step (1) and/or the distillation step (s) (the first distillation step (3) and/or the second distillation step (6)).

Recycling valuable resources (useful components such as DME) from the noncondensable gas (off-gas) to the reaction system provides the effective utilization of the useful components in the reaction system (for example, the components such as DME are utilizable as raw materials of acetic acid) with reducing the loss of the useful components. Recycling such components to the second distillation step (6) improves the removal or separation efficiency of impurities such as acetaldehyde and makes the pressure of the distillation column (6) controllable. Further, recycling the useful components from the noncondensable gas (off-gas) to the first distillation step (3), for example, the upstream side of the first distillation column (3) or at least one condenser C4, improves the liquid-liquid separation in the decanter (5).

In the off-gas treatment step (10) using the scrubber unit, the noncondensable gases 14, 27, 35 (and the nonliquefied component in the decanter (5)), 60, and 71 (and optionally the off-gas from the extraction step (7)), which are produced from the process as described above, may be brought into contact with the absorption solvent (for example, acetic acid) in the absorption column for scrubbing to separate the gases into a first overhead stream and a bottom acetic acid stream; the first overhead stream is rich in carbon monoxide, hydrogen, carbon dioxide, and nitrogen, and the bottom acetic acid stream is rich in acetic acid, methyl iodide, methyl acetate, and methanol. The first overhead stream, rich in carbon monoxide, may be recycled to the reactor (1) and/or the flasher (2).

The bottom acetic acid stream may be distilled and stripped in a diffusion column (a stripping column) to form a second overhead stream and a bottom acetic acid stream; the second overhead stream is rich in methyl iodide and acetic acid (also contains dimethyl ether, methanol, methyl acetate, acetaldehyde, or other compounds), and the bottom acetic acid stream is rich in acetic acid, methyl acetate, and water. The second overhead stream may be cooled and condensed in a condenser to form a noncondensable gas and a condensate. The noncondensaable gas, which is a stream being rich in methyl iodide and carbon monoxide and also containing dimethyl ether, methyl acetate, or other compounds, may be recycled to the reaction step (1) and/or the distillation step (s) (the first distillation step (3) and/or the second distillation step (6)) directly or indirectly. The condensate, which is a stream being rich in methyl iodide, acetic acid, and methyl acetate and also containing dimethyl ether, water, or other compounds, may be recycled to the reaction step (1) and/or the distillation step (s) (the first distillation step (3) and/or the second distillation step (6)) directly or indirectly via the hold tank 25, the condenser C4, the decanter (5), or others. Such recycling to the reaction step (1) provides the effectively utilization for the reaction of the useful components such as methyl iodide, dimethyl ether and methyl acetate. Further, even if the noncondensable gas and/or the condensate is recycled to the distillation step, the rise in the internal pressure of the distillation column of the second distillation step (6) can be prevented by using the pressure control unit 68.

Thus the off-gas can be absorption-treated with an absorption solvent to form a stream rich in carbon monoxide and a steam rich in acetic acid, methyl iodide, and methyl acetate.

The noncondensable gas 14 from the reactor (1) may be scrubbed with an absorption solvent in a high-pressure absorption column. The noncondensable gas 27 from the flasher (2), the noncondensable gas 35 which has not been liquefied in condenser C4 of the first distillation step (3) (and the nonliquefied component in the decanter (5)), and the noncondensable gases 60, 71 from the second distillation step (6) (optionally the off-gases from the water extractors 8, 9) may be scrubbed with an absorption solvent in a low-pressure absorption column.

For the high-pressure absorption column, the flow rate ratio of the noncondensable gas relative to the absorption solvent on the basis of weight may be, for example, about 1/100 to 1000/1, preferably about 1/10 to 100/1, more preferably 1/1 to 50/1, and about 5/1 to 30/1. The absorption solvent may have a temperature of, for example, about 10 to 70° C., preferably about 20 to 60° C., and more preferably about 30 to 55° C. The internal temperature of the high-pressure absorption column is not particularly limited to a specific one, and the column top temperature may, for example, be about 10 to 75° C., preferably about 20 to 60° C., and more preferably about 30 to 55° C., or the column bottom temperature may, for example, be about 10 to 80° C., preferably about 20 to 70° C., and more preferably about 30 to 60° C. (e.g., about 40 to 55° C.). The high-pressure absorption column may have a pressure (gauge pressure) of, for example, about 0.5 to 5 MPa, preferably about 1 to 4 MPa, and more preferably about 2 to 3.5 MPa (e.g., about 2.5 to 3 MPa).

For the low-pressure absorption column, the flow rate ratio of the noncondensable gas relative to the absorption solvent on the basis of weight may be, for example, about 1/100 to 1000/1, preferably about 1/10 to 100/1, more preferably about 1/4 to 30/1, and about 2/1 to 10/1. The temperature of the absorption solvent may, for example, be about 0 to 60° C., preferably about 10 to 50° C., and more preferably about 20 to 40° C. The internal temperature of the low-pressure absorption column is not particularly limited to a specific one, and the column top temperature may, for example, be about 10 to 50° C., preferably about 15 to 40°

C., and more preferably about 20 to 30° C., or the column bottom temperature may, for example, be about 15 to 60° C., preferably about 20 to 50° C., and more preferably about 30 to 40° C. The low-pressure absorption column may have a pressure (gauge pressure) of, for example, about 0.0 to 0.3 MPa (e.g., about 0.0 to 0.25 MPa) and preferably about 0.1 to 0.2 MPa.

The internal temperature of the diffusion column (stripping column) is not particularly limited to a specific one, and the column top temperature may, for example, be about 50 to 150° C., preferably about 70 to 130° C., and more preferably about 90 to 120° C., or the column bottom temperature may, for example, be about 75 to 200° C., preferably about 100 to 180° C., and more preferably about 120 to 160° C. The pressure (gauge pressure) of the diffusion column (stripping column) may, for example, be about 0.0 to 0.3 MPa (e.g., about 0.0 to 0.25 MPa) and preferably about 0.0 to 0.2 MPa. As the absorption solvent, methanol may be used in place of acetic acid or in combination with acetic acid.

Recycle of Process Stream

In the present invention, the process stream which is formed in the separation step and has a reduced acetaldehyde concentration (a process stream obtained by removing acetaldehyde from the volatile phase and/or the succeeding process stream) may be recycled to the reactor. Such a recycling step enables the acetaldehyde concentration of not more than 400 ppm by weight (e.g., 0 or detection limit to about 300 ppm by weight) and preferably about 10 to 250 ppm by weight (e.g., about 20 to 200 ppm by weight) to be maintained in the reaction medium in the reactor.

Recycling the process stream from which acetaldehyde has been removed to the reactor also enables a decrease in the amount of by-product propionic acid. A simple purification of the crude acetic acid stream (3B) also enables the propionic acid concentration of not more than 200 ppm by weight (e.g., detection limit to about 150 ppm by weight or less, preferably about 5 to 100 ppm by weight or less, and more preferably about 10 to 75 ppm by weight or less) to be maintained in purified acetic acid. For example, the crude acetic acid stream (3B) is subjected to a light end distillation column for removing a lower boiling point component and a heavy end distillation column for removing a higher boiling point component and optionally an ion exchange treatment to give a purified acetic acid. According to the present invention, only by distilling the crude acetic acid stream (3B) with the light end distillation column (dehydration column) for removing a lower boiling point component (mainly water), the concentration of propionic acid in the resulting purified acetic acid can be made within the range of the product standard, and it is thus unnecessary to remove a higher boiling point component (such as propionic acid) by the succeeding heavy end distillation column. The purified acetic acid may have a potassium permanganate test value maintained to not less than 120 minutes (e.g., about 150 to 500 minutes, preferably about 200 to 450 minutes, and more preferably about 240 to 400 minutes), and may also have a iodide concentration maintained to not more than 100 ppb (e.g., detection limit to about 75 ppb, preferably about 1 to 50 ppb, and more preferably about 5 to 30 ppb).

Further, an ion exchange treatment of the above-mentioned purified acetic acid stream (for example, passing the acetic acid through an ion exchange resin of which some or all of active sites have been replaced with or exchanged for silver, mercury, and/or copper with stepwise increasing the temperature) removes a $C_{1-15}$alkyl iodide such as hexyl iodide in the acetic acid to not more than detection limit with preventing a loss of silver or others by outflow.

As described above, in the process shown in FIG. 1, the overhead (or distillate) from the first distillation column may be a homogeneous liquid or a biphasic (or two-phase) liquid. Moreover, in the second distillation step, the overhead (or distillate) from the distillation column may also be a homogeneous liquid or a biphasic (or two-phase) liquid.

EXAMPLES

The following examples are intended to describe this invention in further detail and should by no means be interpreted as defining the scope of the invention.

Comparative Example 1

In a flow chart shown in FIG. 1, a pressure control unit was not disposed at a third distillation column (6b). A reactor containing 10 L of a reaction liquid was used for continuously producing acetic acid at a reaction pressure of 2.76 MPaG and a reaction temperature of 186.8° C. The reaction liquid (liquid phase) had a water concentration of 2.7% by weight, a methyl acetate concentration of 1.6% by weight, a methyl iodide concentration of 8.2% by weight, a lithium iodide concentration of 12.3% by weight, and a rhodium concentration of 910 ppm. The gaseous phase in the reactor had a hydrogen ($H_2$) partial pressure of 0.07 MPa.

Although the operation of the third distillation column was tried at a column top pressure (gauge pressure) of 0.18 MPaG, the column top pressure rose to 0.2 MPaG or more, and thus the operation was discontinued from the viewpoint of the withstanding pressure of the apparatus.

Example 1

In a flow chart shown in FIG. 1, a pressure control unit 68 was disposed at a third distillation column (6b), and the column top pressure (gauge pressure) of the third distillation column (6b) was controlled to 0.18 MPaG. In the same manner as Comparative Example 1, acetic acid was produced continuously. Stable continuous production of acetic acid succeeded. The following table shows compositions of a feed liquid 45, via the second distillation column (6a) and line 59, fed to the third distillation column (6b), a distillate (a condensate of an overhead (6A)) 67, a nitrogen gas ($N_2$) 72, and an off-gas 71.

TABLE 1

| | | Feed liquid | Distillate | $N_2$ | Off-gas |
|---|---|---|---|---|---|
| Methyl iodide | wt % | 88.0 | 49.4 | 0 | 25.4 (7.57 vol %) |
| Water | wt % | 0.53 | 0.93 | 0 | 0.15 (0.35 vol %) |
| Methyl acetate | wt % | 9.3 | — | 0 | 0.05 (0.03 vol %) |
| Acetic acid | wt % | 1.8 | — | 0 | 0 |
| Acetaldehyde | wt % | 0.14 | 47.1 | 0 | 32.8 (31.5 vol %) |

TABLE 1-continued

|  |  | Feed liquid | Distillate | $N_2$ | Off-gas |
|---|---|---|---|---|---|
| Methanol | wt % | 0.11 | 0.13 | 0 | 0.01 (0.02 vol %) |
| Dimethyl ether | wt % | 0.0048 | 1.2 | 0 | 3.13 (2.87 vol %) |
| $N_2$ | wt % | — | — | 100 | 38.3 (57.6 vol %) |
| Others | wt % | 0.1552 | 1.24 | 0 | 0.13 (0.06 vol %) |
| Total | wt % | 100 | 100 | 100 | 100 (100 vol %) |
| Flow rate | kg/H | 3.5 | 0.0062 | 0.00047 (0.38 NL/H) | 0.0012 (0.63 NL/H) |
| Temperature | ° C. | — | 38 | 24 | 24 |

Example 2

In a flow chart shown in FIG. 1, a pressure control unit 68 was disposed at a third distillation column (6), and the column top pressure (gauge pressure) of the third distillation column (6) was controlled to 0.18 MPaG. In the same manner as Comparative Example 1, acetic acid was produced continuously. Stable continuous production of acetic acid succeeded. The following table shows compositions of a feed liquid 45, via the second distillation column (6a) and line 59, fed to the third distillation column (6b), a distillate (a condensate of an overhead (6A)) 67, a nitrogen gas ($N_2$) 72, and an off-gas 71.

In Example 2, a cooling water in a condenser C6 has a lower temperature compared with Example 1, and lines 64, 69 and a hold tank 65 have a reduced temperature of 15° C. compared with 24° C. in Comparative Example 1. This causes reduced amounts of methyl iodide, methyl acetate, acetaldehyde, and dimethyl ether in the off-gas of Example 2.

TABLE 2

|  |  | Feed liquid | Distillate | $N_2$ | Off-gas |
|---|---|---|---|---|---|
| Methyl iodide | wt % | 88.0 | 49.4 | 0 | 20.0 (5.38 vol %) |
| Water | wt % | 0.53 | 0.93 | 0 | 0.07 (0.14 vol %) |
| Methyl acetate | wt % | 9.3 | — | 0 | 0.04 (0.02 vol %) |
| Acetic acid | wt % | 1.8 | — | 0 | 0 |
| Acetaldehyde | wt % | 0.14 | 47.1 | 0 | 25.8 (22.3 vol %) |
| Methanol | wt % | 0.11 | 0.13 | 0 | 0.01 (0.01 vol %) |
| Dimethyl ether | wt % | 0.0048 | 1.2 | 0 | 2.71 (2.24 vol %) |
| $N_2$ | wt % | — | — | 100 | 51.3 (69.8 vol %) |
| Others | wt % | 0.1552 | 1.24 | 0 | 0.07 (0.11 vol %) |
| Total | wt % | 100 | 100 | 100 | 100 (100 vol %) |
| Flow rate | kg/H | 3.5 | 0.0062 | 0.00047 (0.38 NL/H) | 0.00087 (0.51 NL/H) |
| Temperature | ° C. | — | 38 | 24 | 15 |

INDUSTRIAL APPLICABILITY

The present invention provides stable production of acetic acid while controlling a pressure of a distillation column. This enables industrially advantageous production of acetic acid with a high purity.

REFERENCE SIGNS LIST

1 . . . Reactor
2 . . . Flash evaporator
3 . . . First distillation column (Splitter column)
5 . . . Decanter
6 (6a, 6b) . . . Second and third distillation columns
8, 9 . . . Extractor

The invention claimed is:

1. A process for producing acetic acid, comprising:
   carbonylating methanol with carbon monoxide in the presence of a catalyst system, acetic acid, methyl acetate, and water, wherein the catalyst system comprises a metal catalyst, an ionic metal iodide, and methyl iodide, to obtain a reaction mixture;
   flash-evaporating the reaction mixture to separate the reaction mixture into a volatile phase and a less-volatile phase;
   first-distilling the volatile phase to separate the volatile phase into a first overhead, a side-cut acetic acid stream and a bottom stream, wherein the first overhead contains at least one permanganate reducing compound (PRC) and methyl iodide, and the PRC contains at least acetaldehyde; and the side-cut acetic acid stream mainly contains acetic acid; and
   separating at least acetaldehyde from the first overhead, wherein the separation comprises:
   second-distilling the first overhead to separate the first overhead into a second overhead rich in acetaldehyde and methyl iodide and a bottom or lower stream, the second distillation comprising at least one distillation column, while controlling an internal pressure of the distillation column in the second distillation by the following method (1) and/or (2):
   (1) introducing at least one gas selected from the group consisting of a nitrogen gas, an off-gas, and an inert gas constantly to the feeding line communicating with the column top of the distillation column, with remaining a control valve on the feeding line open at a predetermined degree of opening,
   (2) discharging or withdrawing a non-condensable gas, and extracting acetaldehyde from the second overhead to form an extract rich in acetaldehyde and a raffinate rich in methyl iodide.

2. The process according to claim 1, wherein the separation further comprises:
condensing the first overhead to form a two-phase first condensate, wherein at least a portion of an upper phase, a lower phase, or both is distilled in the second distillation while controlling the internal pressure of the distillation column.

3. The process according to claim 2, wherein at least a portion of at least the lower phase is distilled in the second distillation while controlling the internal pressure of the distillation column.

4. The process according to claim 1, wherein the first overhead is distilled in the second distillation while controlling the internal pressure of the distillation column to 0.1 to 0.7 MPa.

5. The process according to claim 1, wherein the control of the internal pressure of the distillation column comprises:
detecting the internal pressure of the distillation column by a pressure sensor to obtain a detected value,
producing a controlling signal based on the detected value and a standard value, and
providing or sending the control signal from a pressure control unit disposed at a top of the distillation column to a pressure control valve to regulate or control an opening degree of the pressure control valve for regulating an outflow rate of the first overhead.

6. The process according to claim 1, wherein the second distillation comprises a plurality of distillation steps, and the first overhead is distilled while controlling an internal pressure of the distillation column in at least a downstream distillation step.

7. The process according to claim 1, which further comprises:
condensing the second overhead to form a second condensate and an off-gas, wherein the second condensate is subjected to the extraction and
directly or indirectly recycling a useful component in the off-gas to at least one selected form the group consisting of the carbonylation reaction, the first distillation, and the second distillation.

8. The process according to claim 7, wherein the off-gas is condensed to form a third condensate, and the third condensate is recycled to at least one selected from the group consisting of the carbonylation reaction, the first distillation, and the second distillation.

9. The process according to claim 1, wherein an off-gas produced from the process is recycled to at least one selected from the group consisting of the carbonylation reaction, the first distillation, and the second distillation.

10. The process according to claim 7, wherein the off-gas is adsorbed to an absorption solvent under an applied pressure, and at least one component selected from the group consisting of methyl iodide, methyl acetate, dimethyl ether, water, and carbon monoxide is diffused from the resulting absorption solvent and is recycled to at least one selected from the group consisting of the carbonylation reaction, the first distillation, and the second distillation.

11. The process according to claim 1, wherein at least a portion of the raffinate is recycled to at least one selected from the group consisting of the carbonylation reaction, the first distillation, and the second distillation.

12. The process according to claim 1, wherein the second overhead is subjected to water extraction stepwise or continuously with a plurality of theoretical stages.

13. The process according to claim 1, which further comprises:
fourth-distilling the extract to form a fourth overhead containing an aldehyde and a bottom or lower aqueous stream,
wherein the aqueous stream is used for extraction in the extraction.

14. The process according to claim 1, wherein an acetaldehyde concentration in a reaction medium in a reactor of the carbonylation reaction is maintained at not more than 400 ppm by weight, and
the process further comprises distilling the side-cut acetic acid stream and separating the side-cut acetic acid stream into a purified acetic acid and at least one component selected from the group consisting of a lower boiling point component and a higher boiling point component, wherein at least one of the following (i) to (iii) is satisfied: (i) a potassium permanganate test value of the purified acetic acid is maintained at not less than 120 minutes, (ii) a propionic acid concentration of the purified acetic acid is maintained at not more than 200 ppm by weight, and (iii) an iodide concentration of the purified acetic acid is maintained at not more than 100 ppb.

15. The process according to claim 1, wherein in the method (1), the internal pressure of the distillation column is controlled by introducing at least one gas selected from the group consisting of a nitrogen gas, an off-gas, and an inert gas with a flow rate of not more than 1% relative to a flow rate of the first overhead being fed to the distillation column in the second distillation.

16. The process according to claim 1, wherein in the method (2), the internal pressure of the distillation column is controlled by regulating or controlling the temperature and/or the flow rate of a cooling water for a condenser, which cools and condenses an overhead from the distillation column in the second distillation, to form a condensate and a noncondensable gas, and by regulating or controlling a discharging amount of the noncondensable gas from a discharging line.

17. The process according to claim 1, wherein in the method (2), the inner pressure of the distillation column is controlled by detecting a pressure and/or a flow rate at a withdrawing port communicating with a gaseous phase in a hold tank, which is disposed downstream of a condenser for cooling and condensing an overhead from the distillation column in the second distillation to form a condensate and a noncondensable gas, and regulating or controlling a discharge amount of the noncondensable off-gas.

\* \* \* \* \*